United States Patent
Nabutovsky et al.

(10) Patent No.: US 9,427,595 B2
(45) Date of Patent: Aug. 30, 2016

(54) NEUROSTIMULATION PATCH (71) Applicant: PACESETTER, INC., Sylmar, CA (US)

(72) Inventors: Yelena Nabutovsky, Sunnyvale, CA (US); Melanie Goodman Keiser, McKinney, TX (US); Gene A. Bornzin, Simi Valley, CA (US)

(73) Assignee: PACESETTER, INC., Sylmar, CA (US)

( * ) Notice: Subject to any disclaimer, the term of this patent is extended or adjusted under 35 U.S.C. 154(b) by 96 days.

(21) Appl. No.: 13/938,828

(22) Filed: Jul. 10, 2013

(65) Prior Publication Data
US 2015/0018598 A1    Jan. 15, 2015

(51) Int. Cl.
| | |
|---|---|
| *A61N 1/375* | (2006.01) |
| *A61N 1/36* | (2006.01) |
| *A61N 2/00* | (2006.01) |
| *A61N 2/02* | (2006.01) |
| *A61N 5/00* | (2006.01) |
| *A61N 5/06* | (2006.01) |
| A61N 1/05 | (2006.01) |
| A61N 1/372 | (2006.01) |

(52) U.S. Cl.
CPC ........... *A61N 1/375* (2013.01); *A61N 1/36017* (2013.01); *A61N 1/36071* (2013.01); *A61N 2/006* (2013.01); *A61N 2/02* (2013.01); *A61N 5/00* (2013.01); *A61N 5/0622* (2013.01); *A61N 1/0551* (2013.01); *A61N 1/37241* (2013.01)

(58) Field of Classification Search
CPC .......................... A61N 1/372; A61N 1/36014
USPC ....................................... 607/45, 139
See application file for complete search history.

(56) References Cited

U.S. PATENT DOCUMENTS

| | | | |
|---|---|---|---|
| 2011/0218590 A1* | 9/2011 | Degiorgio et al. | 607/45 |
| 2013/0096641 A1 | 4/2013 | Strother et al. | |
| 2013/0304175 A1* | 11/2013 | Voegele et al. | 607/149 |

* cited by examiner

*Primary Examiner* — Nicole F Lavert (57) ABSTRACT

A neurostimulation patch is affixed to a patient's skin (e.g., via a medical skin adhesive) and provides stimulation energy for an implanted lead. The patch may be used for SCS trials or other applications where is it desirable to avoid implanting a stimulation device within a patient. Circuitry in the patch generates stimulation signals and couples these signals to the implanted lead. The signals may be coupled to the lead via a direct physical connection or via a wireless connection. In some embodiments, the neurostimulation patch is configured in a manner that enables the patch to be placed immediately above the puncture site where an associated percutaneous lead passes through a patient's skin, thereby protecting the puncture site and facilitating secure routing of the lead.

5 Claims, 11 Drawing Sheets

NEUROSTIMULATION PATCH

TECHNICAL FIELD

This application relates generally to stimulation devices and more specifically, but not exclusively, to a neurostimulation patch.

BACKGROUND

Spinal cord stimulation (SCS) is a known technique for treating pain. For example, SCS may be used in a pain management scheme to treat chronic intractable neuropathic pain, refractory angina pain, or peripheral vascular disease pain. SCS is also being investigated for cardiac applications, such as heart failure and atrial fibrillation.

Prior to implanting an SCS system, a patient may undergo a trial period during which the patient is implanted with a percutaneous lead that is routed from an external stimulation device, into the patient, and to the implant site. The external portion of the lead is made long enough (e.g., a few feet in length) to enable the patient to carry the external stimulation device in a purse or some other type of carrying bag or wear the external stimulation device attached to a belt.

The trial period typically lasts from several days to a month or so, depending on the various factors. During this trial period, there is a risk of infection, for example, at the point the lead enters the patient. In addition, use of the external stimulation device may prove troublesome to the patient due to the length of the external part of the lead. Thus, a need exists for improved techniques for providing a trial SCS system to a patient.

SUMMARY

A summary of several sample aspects of the disclosure follows. This summary is provided for the convenience of the reader to provide a basic understanding of such aspects and does not wholly define the breadth of the disclosure. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later. For convenience, the term some aspects may be used herein to refer to a single aspect or multiple aspects of the disclosure. Similarly, the term some embodiments may be used herein to refer to a single embodiment or multiple embodiments.

The disclosure relates in some aspects to a neurostimulation patch that is configured to be affixed to a patient's skin (e.g., via a medical skin adhesive) and provide stimulation energy for an implanted lead. The patch may be used for trials or other applications where is it desirable to avoid implanting a stimulation device within a patient. The patch may be used for various types of neurostimulation including, for example, SCS, peripheral nerve stimulation (PNS), or occipital nerve stimulation (ONS).

Circuitry in the patch generates stimulation signals (e.g., pulses) and couples these signals to the implanted lead. The signals may be coupled to the lead via a direct physical connection (e.g., through the use of a connector) or via a wireless connection. For a direct physical connection, the implanted lead passes through the patient's skin and is connected to the patch via a connector or other suitable mechanism. For a wireless connection, the lead may be implanted in its entirety, whereby the patch and the lead include wireless (e.g., radiofrequency, optical, or inductive) components that enable the patch to transmit energy to the lead.

In some embodiments, the neurostimulation patch is configured in a manner that enables the patch to be placed immediately above the puncture site where an associated percutaneous lead passes through a patient's skin. For example, the patch may include a central portion for securely routing the lead from the puncture site to a connector, as well as a protective material for protecting the puncture point. In addition, such a patch may include a peripheral portion that fixes the patch to the skin and seals off the puncture site from exposure to the air. Accordingly, such a patch protects the puncture site from infection, facilitates secure routing of the lead, and is more convenient (e.g., comfortable) for a patient.

The patch may also include circuitry for communicating with another external device. For example, the patch may communicate via radiofrequency signaling with a programmer that programs stimulation parameters into the patch or otherwise controls the patch operation. Alternatively and/or in addition, a patch that includes monitoring functionality may communicate with an external monitor device to report the patient's condition to the patient or medical personnel.

In view of the above, a neurostimulation patch constructed in accordance with the teachings herein may take various forms.

In some aspects, a neurostimulation patch for stimulating a nervous system of a patient comprises: a body member comprising a substantially flat bottom portion; a neurostimulation circuit located within the body member and configured to output neurostimulation signals via at least one conductor; and a connector located within the body member and configured to electrically couple the at least one conductor to an implantable lead, wherein the bottom portion of the body member defines an opening for passage of the implantable lead to the connector.

In some aspects, a neurostimulation patch for stimulating a nervous system of a patient comprises: a body member comprising a substantially flat bottom portion; a neurostimulation circuit located within the body member and configured to generate neurostimulation signals; and an output circuit located within the body member and electrically coupled to the neurostimulation circuit, wherein the output circuit is configured to radiate energy based on the neurostimulation signals.

The patch may also include a flexible conductive foil or screen surface electrode that may be located on the bottom of the patch. The foil or screen has a conductive adhesive over the electrode for adhering the patch to the skin. The electrode has a relatively large surface area and allows for stimulation current to be applied between the SCS electrodes and the surface electrode through the conductive adhesive. Conductive adhesives are well known in the art and are used for defibrillator and/or transcutaneous pacing applications.

BRIEF DESCRIPTION OF THE DRAWINGS

These and other aspects of the disclosure will be more fully understood when considered with respect to the following detailed description, the appended claims, and the accompanying drawings, wherein:

In accordance with common practice, the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals may be used to denote like features throughout the specification and figures.

DETAILED DESCRIPTION

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

Figure 1:
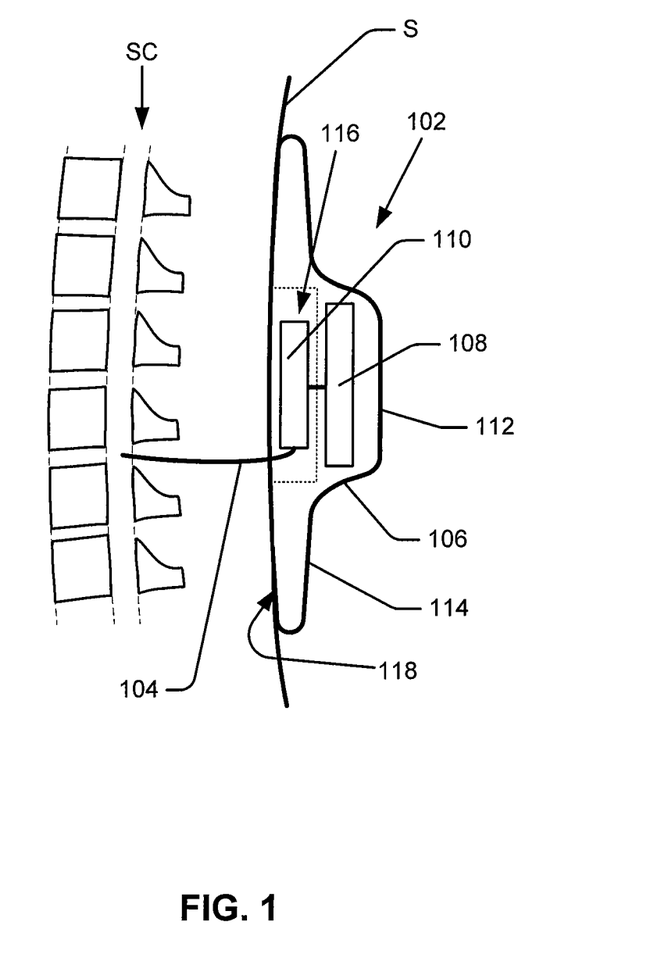
FIG. 1 is a simplified diagram of an embodiment of a stimulation patch that physically connects to a lead.

FIG. 1 illustrates a simplified example of an embodiment of a neurostimulation patch 102 attached to the skin S of a patient and configured to deliver neurostimulation to the spinal cord SC of the patient via a percutaneous lead 104. The patch 102 comprises a body member 106, a neurostimulation circuit 108 located within the body member 106, and a connector 110 located within the body member. As discussed in more detail below, the neurostimulation circuit 108 generates neurostimulation signals (e.g., pulses) that are coupled to the lead 104 via the connector 110. For purposes of illustration, the patch 102 and spine of the patient are shown in cross-sectional view in FIG. 1.

The body member 106 comprises a central portion 112 and a peripheral portion 114. In a typical implementation of the embodiment of FIG. 1, the central portion 112 embodies the circuitry (e.g., the neurostimulation circuit 108 and the connector 110) for the patch 102 and serves to protect the puncture site where the lead 104 passed through the skin S, while the primary function of the peripheral portion 114 is to affix the patch 102 to the skin S and provide a seal.

As discussed in more detail below, circuitry may be distributed in other ways and the portions of the patch may serve different functions in other embodiments of a neurostimulation patch. For example, in various embodiments, electronic circuitry and/or batteries may be contained in a central portion of a patch and/or in a peripheral (e.g., circumferential) portion of a patch.

The bottom portion (left side in FIG. 1) of the body member 106 defines an opening 116 (delineated by the dashed lines) for passage of the lead 104. The opening 116 also serves to protect the puncture site since the body member 106 does not lie directly on the skin at the puncture site in the area of the opening 116 (e.g., the opening provides a space that enables use of a gauze material over the puncture site as discussed below). FIG. 1 shows only one opening 116 but multiple openings 116' (not shown) can provide for passage of multiple leads 104' (not shown) into the patch for connection to the circuitry 108. This allows for covering additional sites along the spinal cord to increase coverage of possible pain relieving tracts along the spinal cord.

In some embodiments, the body member 106 is constructed of a flexible (e.g., pliable) material. Through the use of such a material, the patch 102 may readily conform to the contours of the patient's skin, even when the skin is subjected to movement as the patient moves. Accordingly, the patch 102 may be relatively comfortable for the patient to wear. Examples of a material from which the body member 106 may be constructed include one or more of: flexible molded polymer, silicone, polyurethane, soft poly vinyl chloride (PVC), or butyl rubber. In some embodiments, a portion of the body member 106 (e.g., a portion of the bottom) comprises a conductive polymer to provide at least one surface electrode that contacts the skin S of the patient. This surface electrode may be formed of a metallic foil or screen coated with a conductive adhesive. This can be used for unipolar stimulation to test configurations of stimulation similar to those between the implanted lead and the implantable pulse generator (IPG). This is often described as unipolar stimulation.

In some embodiments, the bottom portion of the body member 106 includes or has attached thereto an adhesive material 118 that will adhere to the patient's skin S. The adhesive material 118 may include a substance (e.g., cortisone) to mitigate inflammatory irritation of the skin and/or a substance (e.g., a topical anesthetic, etc.) to reduce pain, if applicable. One example of an appropriate material is a pressure sensitive adhesive (PSA). PSAs remain flexible after adhesion, which again may help to maintain patient comfort. An adhesive material such as a PSA may be incorporated into or applied to the patch 102 during manufacturing or at a later point in time (e.g., during the surgical implant procedure). Upon implant of the lead 104, the patch 102 is bonded to the patient's skin, upon application of pressure. Other fixation techniques may be used to attach a neurostimulation patch to a patient in other embodiments.

In some embodiments, the patch 102 includes or is combined with absorbing material gauze (e.g., a bandage) for absorbing blood and other body fluids. For example, as discussed in more detail below, a gauze material may be located over the opening 116 to protect the puncture site. The gauze material could have antibacterial qualities. For example, the gauze material could be impregnated with antibiotics, silver, or another anti-bacterial substance.

In some embodiments, other portions of the patch 102 could have antibacterial qualities as well. For example, the body member 106 could be impregnated with antibiotics, silver, or another anti-bacterial substance. Alternatively, the patch 102 could include circuitry to deliver an electric field that prevents formation of a biofilm and thus prevents infection.

In some embodiments, the patch 102 (e.g., the bottom portion of the peripheral portion 114) includes a seal around the puncture site and/or around the patch 102. Such a seal may protect the puncture site from infection and/or protect the components of the patch 102. In some cases, the seal is waterproof to provide protection from water (e.g., to enable the patient to shower). The seal could be made of a material such as, for example, octyl cyanoacrylate, 2-octyl cyanoacrylate (e.g., Dermabond) or N-butyl-2-cyanoacrylate (e.g., Indermil).

In some embodiments, the electronics of the patch 102 (e.g., the neurostimulation circuit 108 comprising electronic integrated circuits and a battery) could be waterproofed by encasing them in a water-repellent material. This waterproofing may be provided, for example, by a conventional nanocoating that is used on commercial electronics, by sealing the electronics in a waterproof material such as parylene, silicone, etc.

The patch can be disposable or reusable. Also, in some embodiments, the electronics in the patch 102 are removable to enable the patch to be changed and/or the electronics replaced. In the former case, the electronics would be detached from an old patch and then reattached to the new patch. In this way, the patch could be changed every day or as needed. In the latter case, the electronics may be replaced or renewed (e.g., a battery recharged or replaced).

In the example of FIG. 1, the lead 104 may be permanently or releasably connected to the patch 102 via the connector 110.

As an example of a permanent connection, the connector 110 may comprise a set of conductors (e.g., contacts or other types of conductors) to which a comparable set of conductors on the lead 104 (not shown in FIG. 1) may be electrically coupled while providing a substantially permanent (i.e., not readily removable) fixture. For example, the lead conductors may be soldered to contacts of the connector 110.

As an example of a releasable connection, the connector 110 may comprise a releasable connector that includes contacts, whereby the releasable connector is configured to accept a complementary connector (e.g., a set of contacts) on the lead 104 (not shown in FIG. 1). In the case, the lead 104 may be readily connected to or disconnected from the patch 102 to, for example, facilitate implanting the lead 104, changing out the patch 102, or changing out the electronics of the patch 102.

In some embodiments, a neurostimulation patch employs wireless technology instead of a directly coupled electrical connection to transfer stimulation energy to an implanted lead. Here, the patch may include an electromagnetic transmitter circuit that radiates electromagnetic energy with sufficient strength to penetrate the patient's skin and enable a receiver circuit in the lead to receive the energy.

In some embodiments, the patch will have a toroidal coil having an axis that is substantially perpendicular to the skin. The coil will be mutually inductively coupled to a substantially toroidal coil that is electrically attached to the distal portion of the lead beneath the skin. When the coil in the patch is then driven with an electric current, mutual inductance causes current to flow through the subcutaneous coil located beneath the skin. The subcutaneous coil is electrically connected to the SCS electrodes. The mutual inductive coupling is optimized by the two coils having a common axis and being in close proximity. So the patch coil should be aligned axially with the subcutaneous coil.

In some embodiments, a neurostimulation patch communicates with an implanted lead optically. The implanted lead would contain a photodetector on the proximal end. At implant, once the lead is placed, the proximal end with the photodetector would be left close to the skin surface, subcutaneously. The patch would contain light transmitters, such as LEDs. The patch would transmit power for pacing through this optical connection.

In some embodiments, a neurostimulation patch communicates with an implanted lead via radiofrequency (RF) signals. In this case, the patch includes an RF transmitter and the lead includes an RF receiver on its proximal end. Upon implant, the transmitter and receiver would typically be placed relatively close to one another in a similar manner as the optical embodiment described above.

In some embodiments, a patch communicates with an implanted lead via inductive communication. In this case, the patch includes an inductive energy transmitter and the lead includes an inductive energy receiver on its proximal end. Upon implant, the transmitter and receiver would typically be placed relatively close to one another in a similar manner as the optical embodiment described above.

The use of wireless technology may provide several advantages over wired technology. For example, the percutaneous lead may be entirely implanted. Consequently, the puncture site is able to heal, thereby eliminating the need to protect the puncture site once it heals. In addition, external lead routing issues are avoided in this case. Moreover, once a trial period is over, an implanted lead would not have to be replaced since it would not have been externalized. Rather, the implanted lead could simply be coupled to a permanently implanted stimulation energy source. For example, the proximal end of the lead may be connected (e.g., optically, via RF, etc.) to a permanently implanted stimulation system. Alternatively, the lead may be physically connected to an extension leading to a permanently implanted stimulation system.

Figure 2:
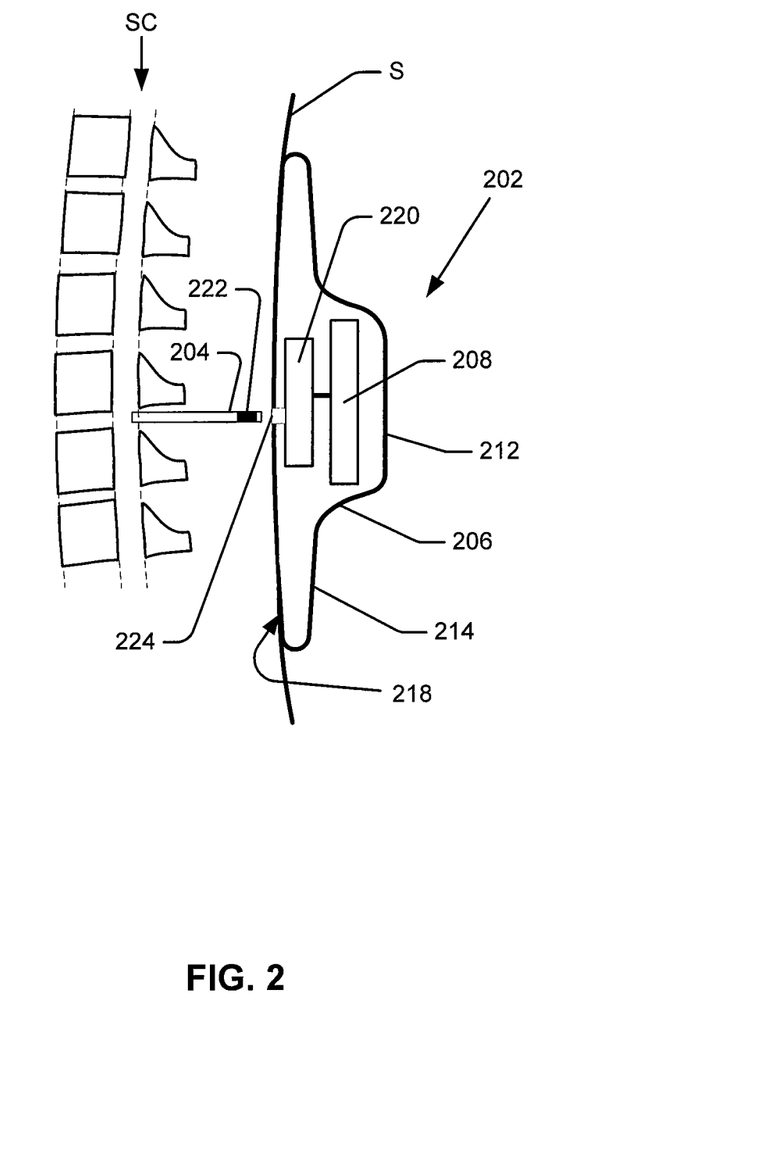
FIG. 2 is a simplified diagram of an embodiment of a stimulation patch that transfers energy to a lead via wireless technology.

FIG. 2 illustrates a simplified example of an embodiment of a neurostimulation patch 202 that employs wireless technology to transfer stimulation energy to a percutaneous lead 204. As in the example of FIG. 1, the patch 202 is attached to the skin S of a patient and the lead 204 delivers neurostimulation to the spinal cord SC of the patient.

The patch 202 comprises a body member 206, a neurostimulation circuit 208 located within the body member 206, and an output circuit 220 located within the body member 206. The neurostimulation circuit 208 generates neurostimulation signals (e.g., pulses) that are sent to the output circuit 220 (e.g., via a conductor).

The output circuit 220 is configured to radiate energy (e.g., electromagnetic energy such as light, RF energy, or inductive energy) based on the neurostimulation signals. For example, the output circuit 220 may comprise a radiofrequency generator circuit configured to radiate radiofrequency energy based on the neurostimulation signals. As another example, the output circuit 220 may comprise an electromagnetic induction circuit configured to radiate electromagnetic induction energy based on the neurostimulation signals. As yet another example, the output circuit 220 may comprise an optical transmitter circuit configured to radiate optical energy based on the neurostimulation signals. In this case, the bottom portion of the body member 206 may include a lens 224 to facilitate transmission of light from the optical transmitter circuit through the patient's skin S.

The proximal portion of the lead 204 includes a receiver circuit 222 that is configured to receive the energy radiated by the output circuit 220. Suitable structure in the lead 204 transfers this energy or energy derived there from to the implant site at or near the patient's nervous system (the spinal cord SC in the example of FIG. 2). For example, the receiver circuit 222 may generate electrical signals based on the received energy, whereby electrical conductors (not shown) in the lead 204 transfer these electrical signals to electrodes (not shown) at the distal portion of the lead 204.

Similar to the patch of FIG. 1, the body member 206 comprises a central portion 212 and a peripheral portion 214. In various embodiments, electronic circuitry and/or batteries may be contained in a central portion 212 of the patch 202 and/or in the peripheral portion 214 of the patch 202. In a typical implementation, the peripheral portion 214 serves to fix the patch 202 to the skin S and provide a seal.

Other aspects of the patch 202 may be similar to the patch 102. For example, the body member 206 may be constructed of a flexible material. In addition, the bottom portion of the body member 206 may include or have attached thereto an adhesive material 218 that will adhere to the patient's skin without irritating the skin. Also, portions of the patch 202 could have antibacterial qualities. Furthermore, the patch 202 (e.g., the bottom portion of the peripheral portion 214) may include a seal to protect the components of the patch 202.

Figure 3:
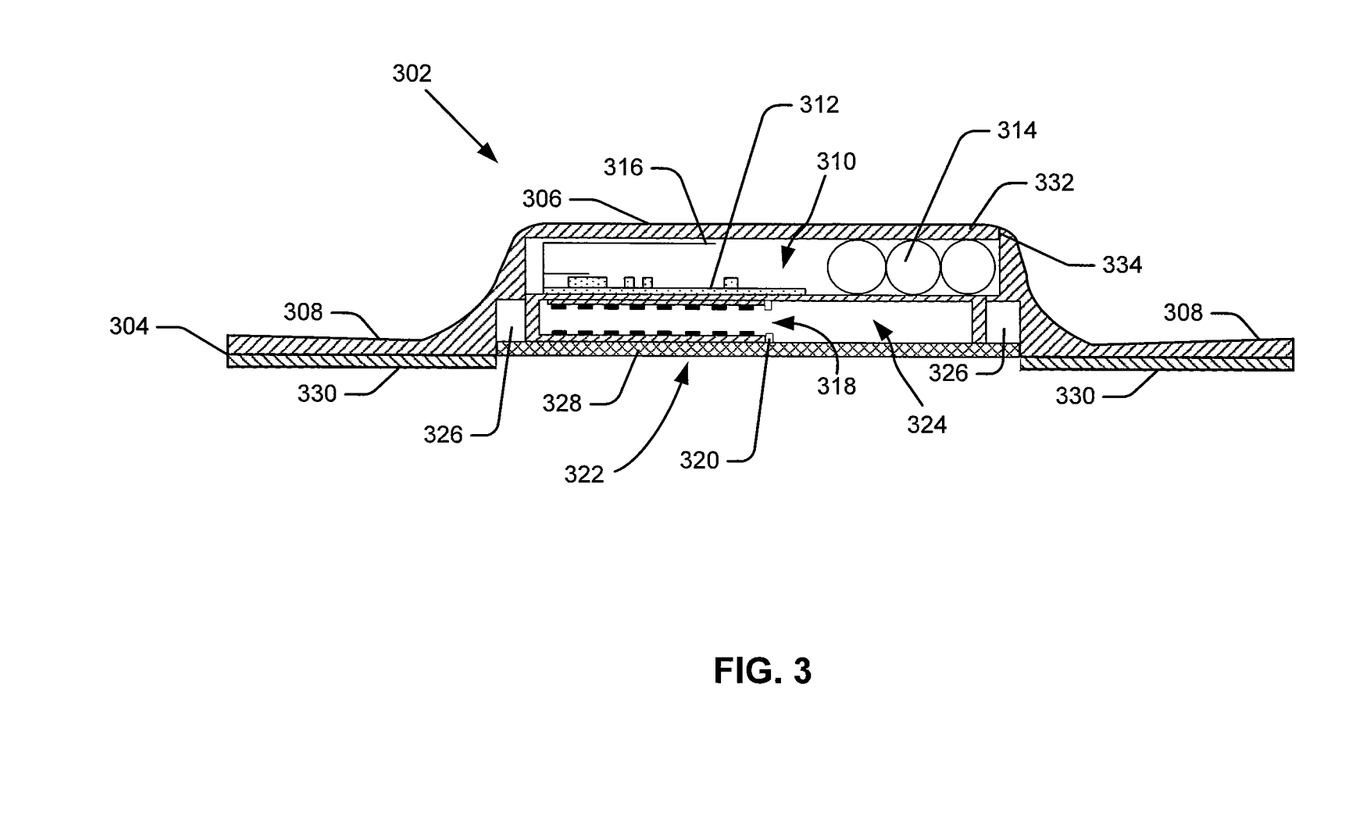
FIGS. 3, 4, and 5 are simplified diagrams of an embodiment of a stimulation patch, illustrating additional details.
Figure 4:
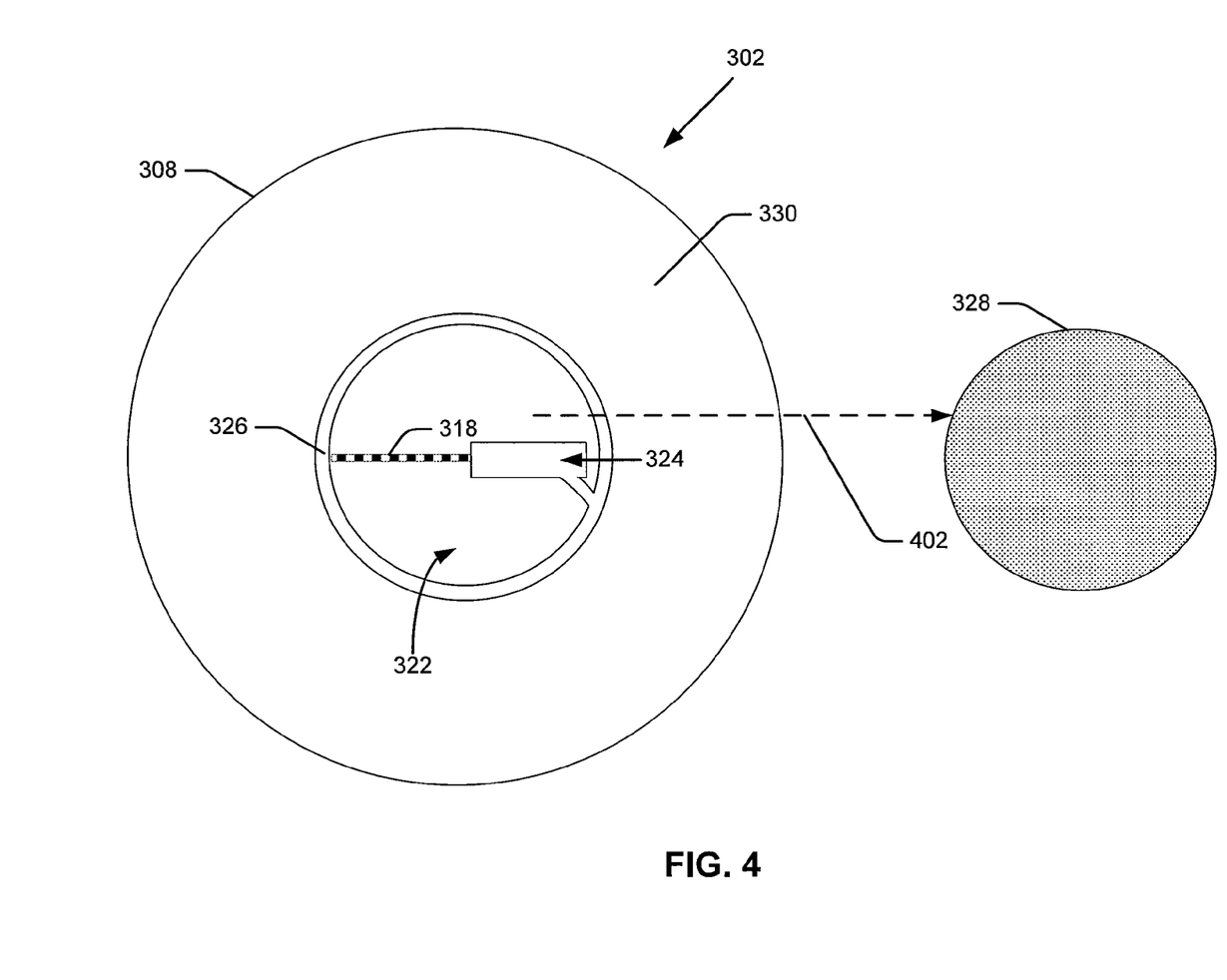
Figure 5:
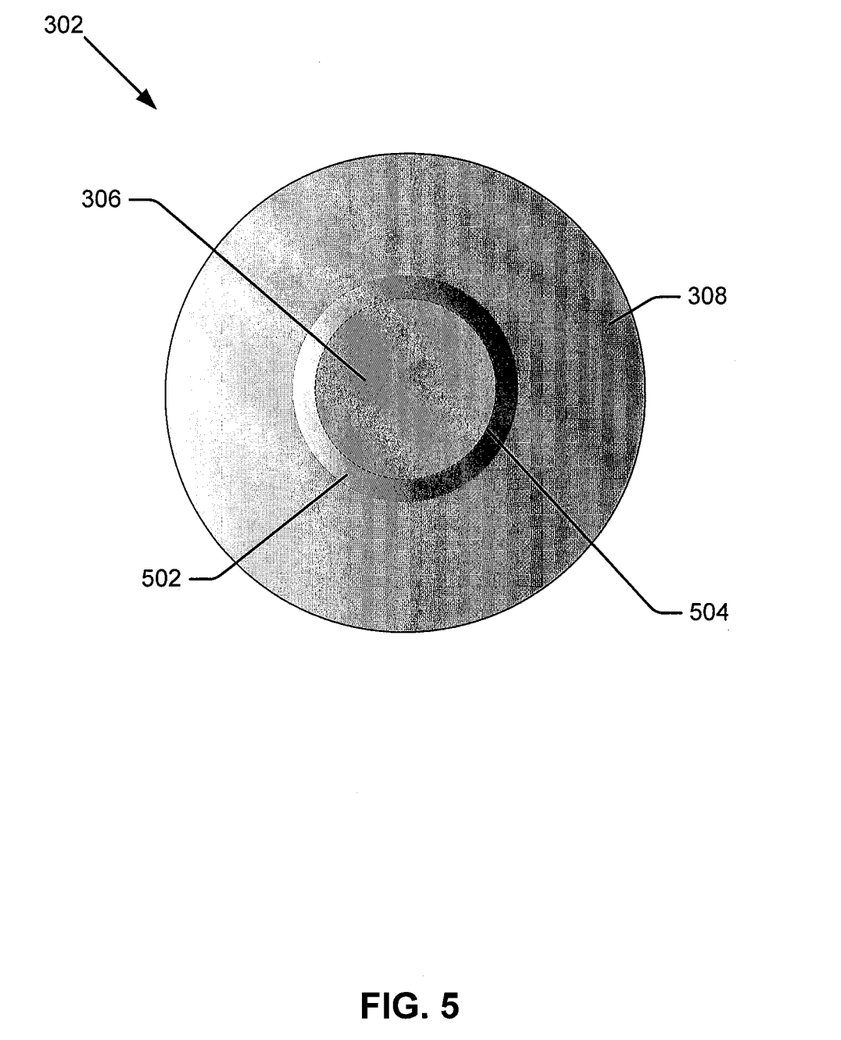

Referring to FIGS. 3-5, several aspects of a neurostimulation patch 302 constructed in accordance with the teachings herein will be treated in more detail. FIG. 3 illustrates a cross-sectional view, FIG. 4 illustrates a bottom view, and FIG. 5 illustrates a top view.

The patch 302 comprises a body member 304 having a central portion 306 and a peripheral portion 308. The body member 304 defines a chamber 310 for holding a circuit 312 (in this example, a circuit board with integrated circuit components) comprising a neurostimulation circuit, and for holding a battery circuit 314. The battery circuit 314 includes at least one battery (in this example, 3 batteries) and, in some embodiments, circuitry for recharging the battery (e.g., an induction coil, rectifier circuitry, and filter circuitry). The circuit 312 is coupled to an antenna 316 for communication with an external device (not shown).

In the example of FIG. 3, the patch 302 employs a releasable connector 318 that is configured to accept an implantable lead (not shown). The connector 318 is electrically coupled to the circuit 312 to receive stimulation signals. In some embodiments, the connector 318 comprises a set of connector contacts on a printed wiring board. The connector 318 also includes a lead seal 320 for sealing the lead once the lead connector (proximal portion of the lead) is inserted into the connector 318. Multiple connectors 318' (not shown) may be coupled to circuit 312 to provide for multiple SCS leads being connected to the patch.

The bottom portion of the body member 304 defines an opening 322 for passage of the implantable lead to the connector 318. One section of the opening 322 provides a passageway 324 to facilitate insertion of the proximal portion of the lead into the connector 318. Another section of the opening 322 provides a trough 326 for wrapping any excess length of the lead. As discussed herein, a gauze material 328 extends across the bottom of the opening 322 to protect the puncture site in the patient's skin (not shown). Also as discussed herein, the bottom portion of the peripheral section 308 comprises (e.g., contains, includes, or has attached thereon) a medical skin adhesive 330. The above aspects of the patch 302 may be better understood by reference to FIG. 4 which shows a bottom view of the patch 302 with the gauze material 328 temporarily removed (as indicated by the dashed arrow 402). The center portion of FIG. 4 depicts a cross-sectional view to better illustrate the above-described aspects of the opening 322.

FIG. 5 illustrates, in a plan view, the transition (represented by the area 502) between the central portion 306 and the peripheral portion 308. In this example, the width of the peripheral portion 308 (as measured from the outer edge of the central portion 306) is slightly less than the width of the central portion 306. As one example, the central portion may have a width (diameter) of 1-1.5 inches (or 3-4 centimeters) or less, while the overall width of the patch 302 may be 2-4 inches (or 5-10 centimeters) or less. It should be appreciated that other sizes and/or shapes may be employed for a patch in accordance with the teachings herein.

FIG. 3 also illustrates that in some embodiments, a top cover member 332 that lies above the chamber 310 may be at least partially removable to allow removal of circuitry (e.g., a neurostimulation circuit and/or batteries) from the chamber 310. For example, the body member 304 may include a seam 334 that enables at least a portion of the top cover member 332 to be lifted up from the body member 304. As one example, the seam 334 may be formed partially or entirely around the circumference of the top of the center portion 305 (e.g., the dashed line 504 in FIG. 5). In some embodiments (e.g., where the patch needs to be waterproof), an appropriate mechanism (e.g., a watertight seal structure or sealant) may be employed to ensure that the seam 334 is sufficiently sealed and/or structurally sound.

As shown in FIG. 3, the bottom portion of the body member 304 may be substantially flat (e.g., less than 30 degree curvature) prior to fixation on a patient (e.g., when the body member 304 is not subjected to external force). Since, the body member 304 is flexible, however, it can curve to better fit the shape of the patient's body, as needed.

Figure 6:
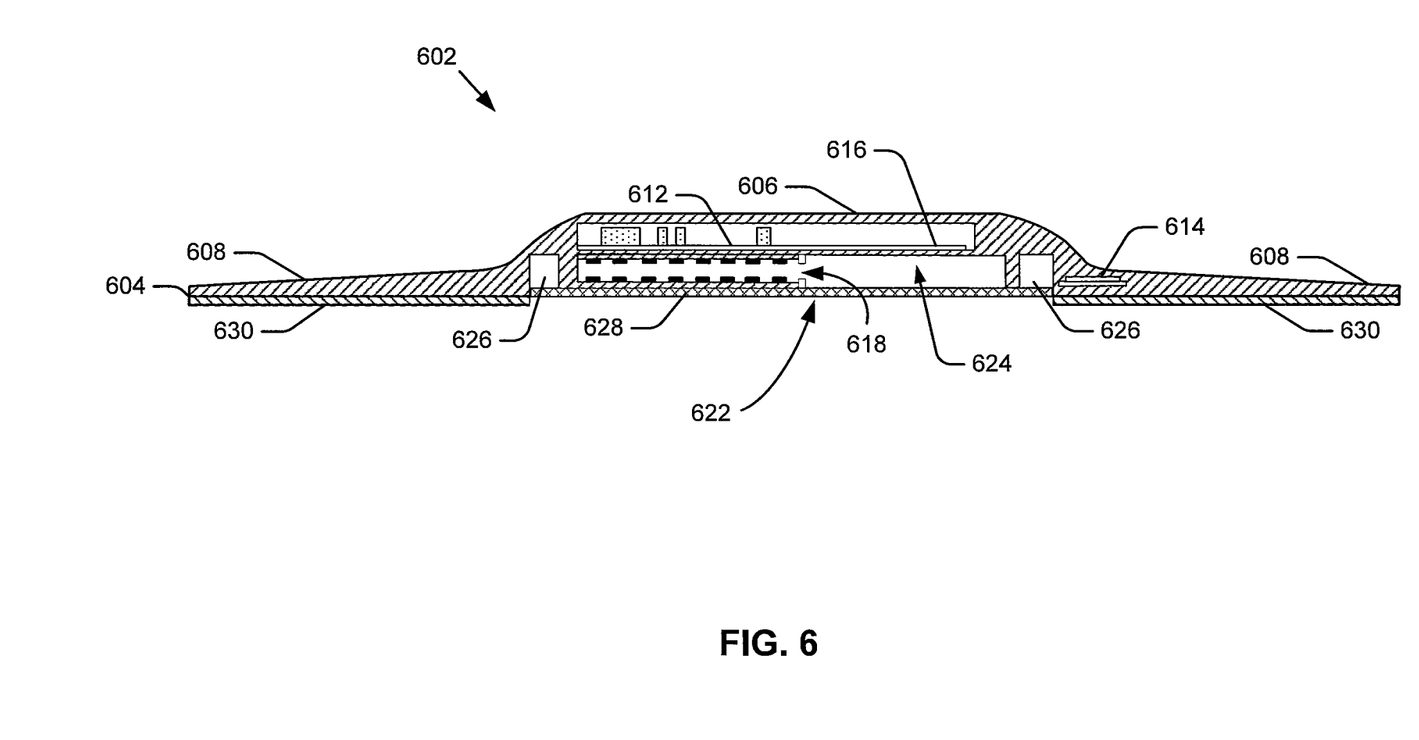
FIG. 6 is a simplified diagram of an embodiment of a stimulation patch that includes circuitry in a peripheral portion of the patch.

In some implementations, it may be desirable for a neurostimulation patch to have a very low profile (e.g., to improve the wearability of the patch). FIG. 6 illustrates an embodiment of a neurostimulation patch 602 that has a lower profile than the patch 302. This lower profile is achieved, in some aspects, through the use of smaller batteries (e.g., "button" cell-type batteries) and by placing at least a portion of the circuitry in the peripheral portion of the patch 602. In this way, a significant reduction in the height of the central portion of the patch 602 may be achieved.

The patch 602 comprises a body member 604 having a central portion 606 and a peripheral portion 608. The body member 604 houses a circuit 612 (in this example, a circuit board with integrated circuit components) comprising a neurostimulation circuit and a horizontally oriented antenna 616. The patch 602 employs a releasable connector 618 that is electrically coupled to the circuit 612 to receive stimulation signals.

Similar to the patch 302, the bottom portion of the body member 604 defines an opening 622 for passage of the implantable lead to the connector 618. The opening 622 also provides a passageway 624 and a trough 626 for routing the lead. A gauze material 628 is provided in the opening 622 and the bottom portion of the peripheral section 608 comprises (e.g., contains, includes, or has attached thereon) a medical skin adhesive 630.

Advantageously, in this embodiment, the battery circuit 614 (in this example, comprising at least one relatively flat cell-type battery) is located at least partially within the peripheral portion 608. It should be appreciated that other circuitry (e.g., an antenna and electronic components) may be located at least partially within the peripheral portion 608 as well.

Through the use of these techniques, the patch 602 may be constructed with a very low profile. As one example, the peripheral portion 608 may have a height of 5 millimeters or less, while the central portion 606 has a height of 1 centimeter or less. Thus, the patch 602 may be substantially flat (e.g., the height of the patch is less than 20% of the width of the patch). It should be appreciated that other sizes and/or shapes may be employed for a patch in accordance with the teachings herein.

Figure 7:
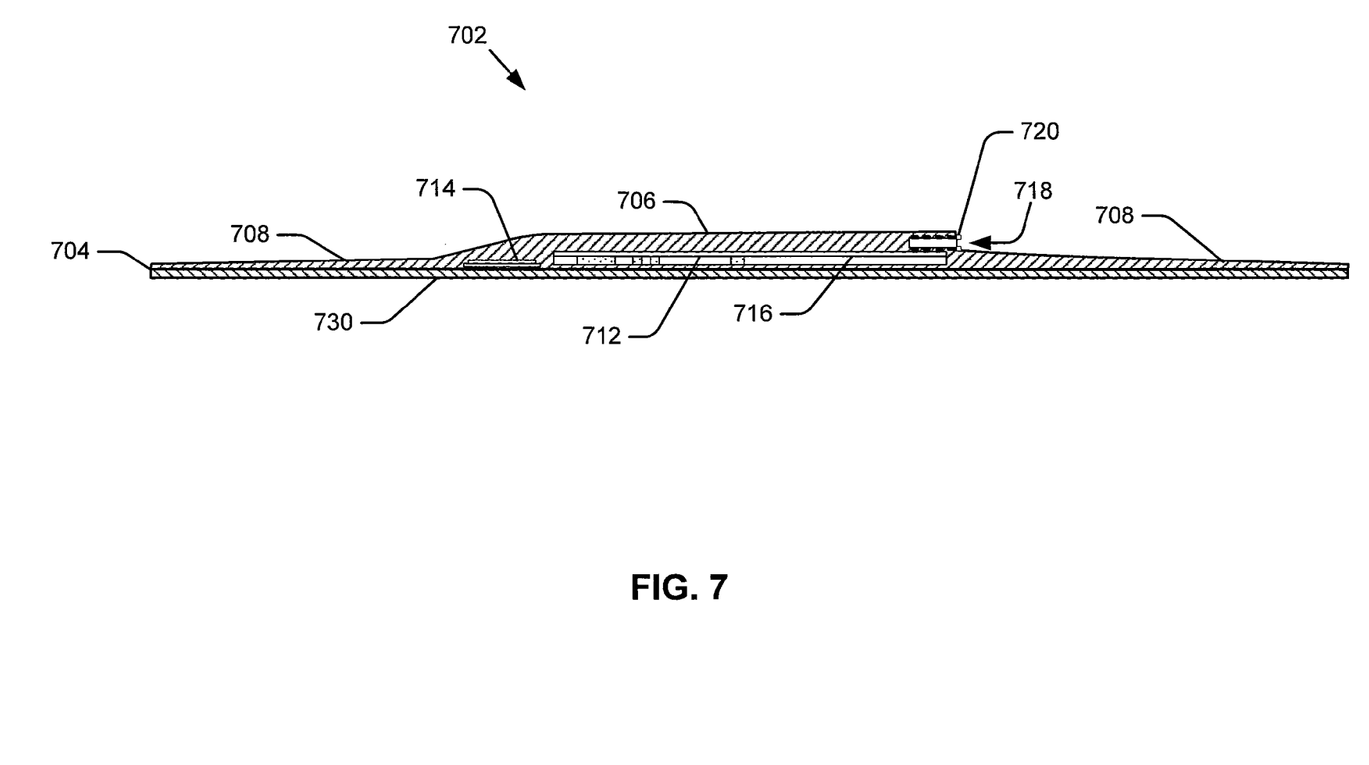
FIG. 7 is a simplified diagram of an embodiment of a stimulation patch that includes a side opening for a connector.

In some embodiments, a neurostimulation patch may be placed remotely from the lead puncture site. In this case, the percutaneous lead may connect to a connector having an opening on the outside of the patch. FIG. 7 illustrates a sample embodiment of this type of neurostimulation patch.

Similar to the patch 602, the patch 702 comprises a body member 704 having a central portion 706 and a peripheral portion 708. The body member 704 houses a circuit 712 (in this example, a circuit board with integrated circuit components) comprising a neurostimulation circuit and an antenna 716. In addition, a battery circuit 714 (in this example, comprising at least one relatively flat cell-type battery) is located at least partially within the peripheral portion 708. Finally, a releasable connector 718 (with an associated lead seal 720) is electrically coupled to the circuit 712 to receive stimulation signals.

In this embodiment, however, the releasable connector 718 is accessed via an opening in the side of the body member 704. Consequently, this embodiment need not employ a bottom opening for routing the lead and the entire bottom portion of the body member 704 may comprise (e.g., contain, include, or have attached thereon) a medical skin adhesive 730. In addition, since the patch 702 is located remotely from the puncture site, the patch 702 need not employ a protective gauze material.

Figure 8:
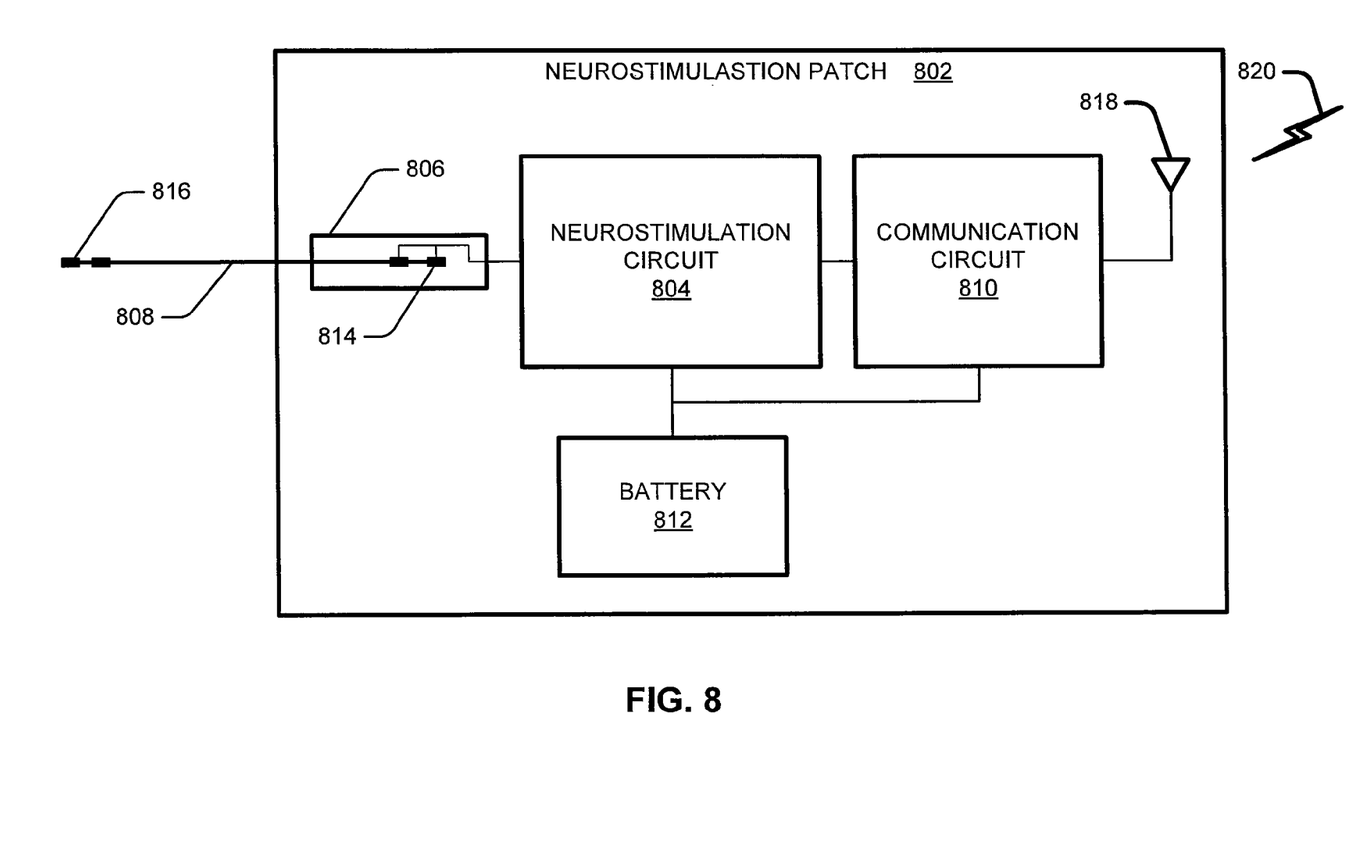
FIG. 8 is a simplified block diagram of an embodiment of stimulation patch that provides neurostimulation for a patient.

FIG. 8 illustrates a simplified high-level example of an embodiment of a neurostimulation patch 802 configured to generate neurostimulation signals. The patch 802 includes a neurostimulation circuit 804 for generating neurostimulation signals, a connector 806 that is connected to one or more implantable leads (hereafter referred to for convenience as the "implantable lead 808"), a communication circuit 810 for communicating with an external device (not shown), and a battery 812.

The neurostimulation circuit 804 includes a signal generator and signal driver circuits (not shown) for generating the neurostimulation signals. The output of the signal generator is coupled to contacts 814 of the implantable lead 808 via the connector 806, whereby generated neurostimulation signals are induced at the designated stimulation sites in the patient (not shown) via electrodes 816 of the implantable lead 808.

The neurostimulation circuit 804 may include a processing system (not shown) that controls the application of neurostimulation. In a typical implementation, neurostimulation is controlled based on signal attributes and timing parameters programmed into a memory device (not shown). Examples of the neurostimulation signal attributes include amplitude, frequency, and pulse shape. In the event neurostimulation is warranted, the processing system generates an indication to control the signal generator to generate a neurostimulation signal that is applied to the nervous system of the patient as discussed herein.

In the example of FIG. 8, the communication circuit 810 (comprising an RF transmitter and RF receiver) transmits and receives RF telemetry signals via an antenna 818 as represented by a signaling waveform 820. In this way, an external device may communicate with the patch 802 (e.g., with the processing system) to send information (e.g., stimulation parameters, on/off commands, etc.) to the patch 802 and/or receive information (e.g., parameters currently in use, stimulation history, etc.) from the patch 802.

The neurostimulation parameters may be specified in various ways. For example, neurostimulation parameters may be downloaded from an external device (e.g., a programmer) into the neurostimulation patch 802 or may be predefined (e.g., programmed into the neurostimulation patch 802 during manufacture).

The size of the battery 812 may depend on the length of time that the patch 802 will be in use. For example, for stimulation trials (e.g., that last a few days, 30 days, or some other relatively short period of time), a relatively small battery will be sufficient to power the patch 802. Consequently, such a battery may be small enough to be relatively flat and fit into either the central portion or even a peripheral portion of the patch 802.

For purposes of illustration, an example of a battery configuration follows. In this example, it is assumed that the stimulation pulse has the following characteristics: a pulse width of 400 microseconds, a constant current of 10 milliamps (mA), and a frequency of 50 Hertz. A lead electrode impedance of 800 ohms is also assumed. If stimulation is applied 24 hours a day, a 43 mA-hour battery will last for 3 days, while a 430 mA-hour battery will last for 30 days. Accordingly, a relatively small battery may provide sufficient power for the patch 802.

The patch 802 may include a permanent battery, a rechargeable battery, or a replaceable battery. In the latter cases, the patch may have a battery compartment so that the battery may be readily replaced.

Figure 9:
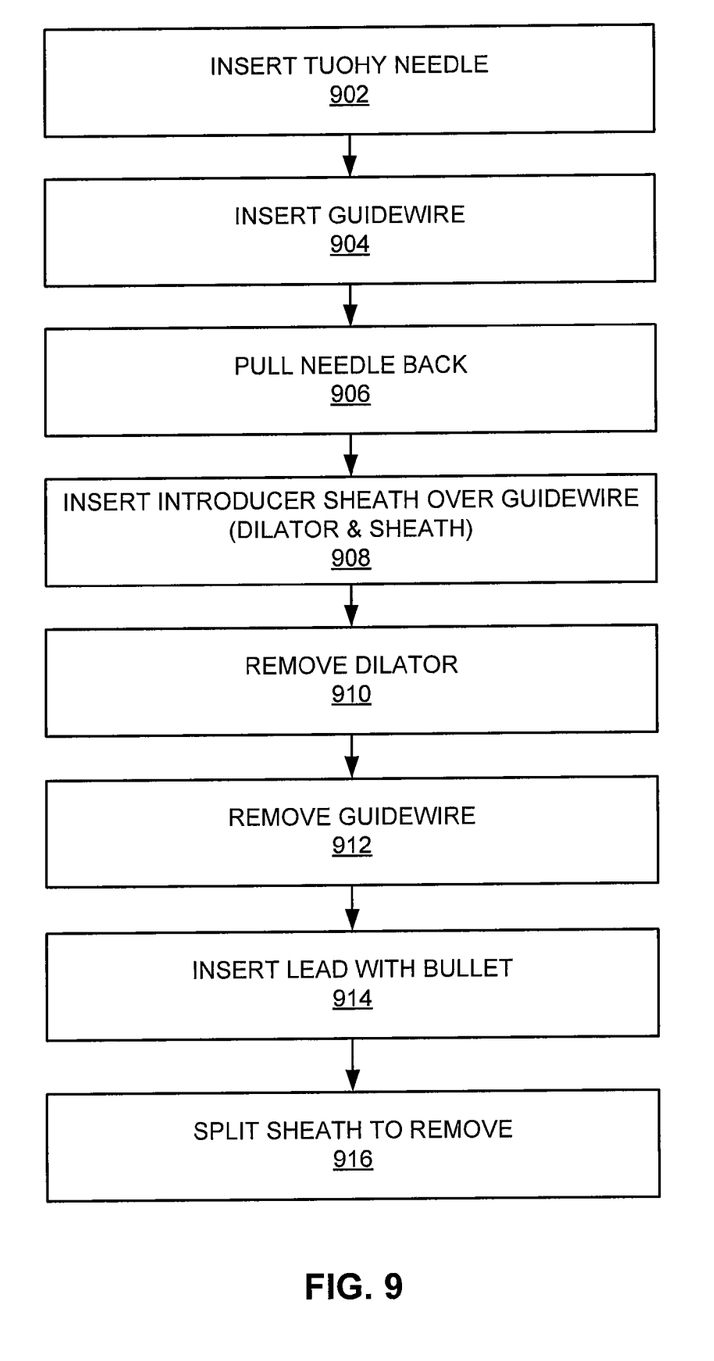
FIG. 9 is a simplified flowchart of an embodiment of operations that may be performed to implant a lead connected to a stimulation patch.
Figure 10:
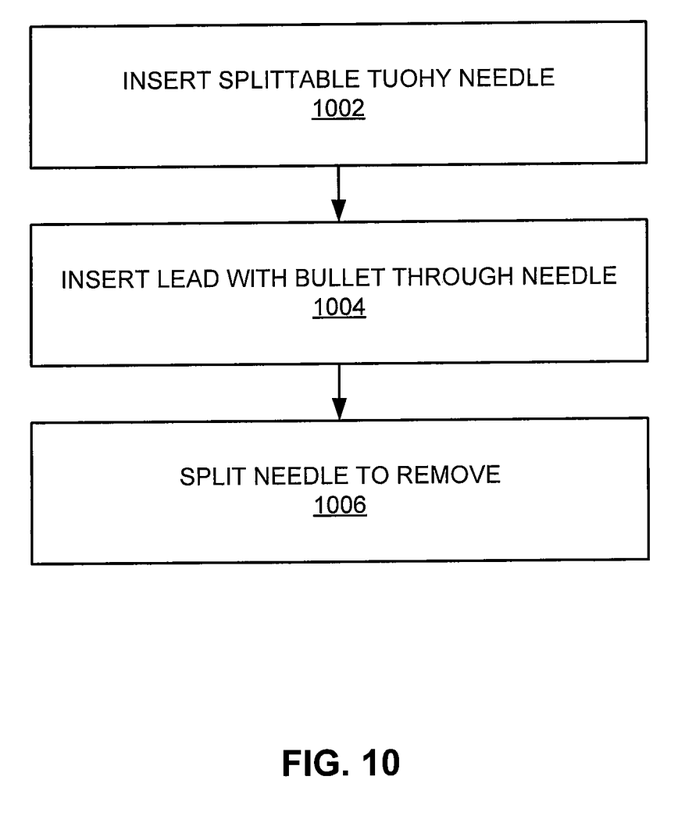
FIG. 10 is a simplified flowchart of another embodiment of operations that may be performed to implant a lead connected to a stimulation patch.

FIGS. 9 and 10 illustrate two examples of how a neurostimulation patch may be placed on a patient in embodiments where the lead is physically and "permanently" attached to the patch (e.g., via a soldered connection). FIG. 9 describes an example of an embodiment that employs a splittable sheath. FIG. 10 describes an example of an embodiment that employs a splittable Tuohy needle.

For convenience, the operations of FIGS. 9 and 10 (or any other operations discussed or taught herein) may be described as being performed by specific components. It should be appreciated, however, that these operations may be performed by other types of components and may be performed using a different number of components. It also should be appreciated that one or more of the operations described herein may not be employed in a given implementation.

Referring initially to FIG. 9, as represented by block 902, a Tuoghy needle is inserted into the patient.

As represented by block 904, a guidewire is inserted into the Tuoghy needle and directed to the implant site.

As represented by block 906, the needle is removed (pulled back), while leaving the guidewire in place.

As represented by block 908, an introducer sheath (having a dilator at its distal end) is inserted over the guidewire.

As represented by block 910, the dilator is removed, while leaving the sheath in place.

As represented by block 912, the guidewire is removed (pulled back), while leaving the sheath in place.

As represented by block 914, the lead (with a patch) is inserted into the sheath and thereby routed to the implant site.

As represented by block 916, once the lead is implanted and secured, the sheath is split (starting at its proximal end) as it is removed, thereby not affecting the patch attached to the proximal end of the lead.

Referring now to FIG. 10, as represented by block 1002, a splittable Tuoghy needle is inserted into the patient and directed to the implant site.

As represented by block 1004, the lead (with a patch) is inserted into the Tuoghy needle and routed to the implant site.

As represented by block 1006, once the lead is implanted and secured, the needle is split (starting at its proximal end) as it is removed, thereby avoiding the patch attached to the proximal end of the lead.

Other techniques for placing a patch on a patient may be employed in cases where the leads are permanently affixed. For example, if very small electronic and battery circuits are used (e.g., for deployments are only used for a few days and thus do not need a large battery), the patch may be very thin and small. In such a case, the patch may be rolled-up (along the axis of the lead) small enough so that the patch will fit through a lead delivery system (e.g., an Epiducer™ sold by St. Jude Medical). That is, the patch could roll up into a cylindrical shape, small enough to fit through the lead delivery system. After implanting the lead, the sheath is removed over the lead and rolled-up patch. The patch would be unrolled after the lead delivery system is removed. The patch may then be affixed to the patient as discussed herein.

Figure 11:
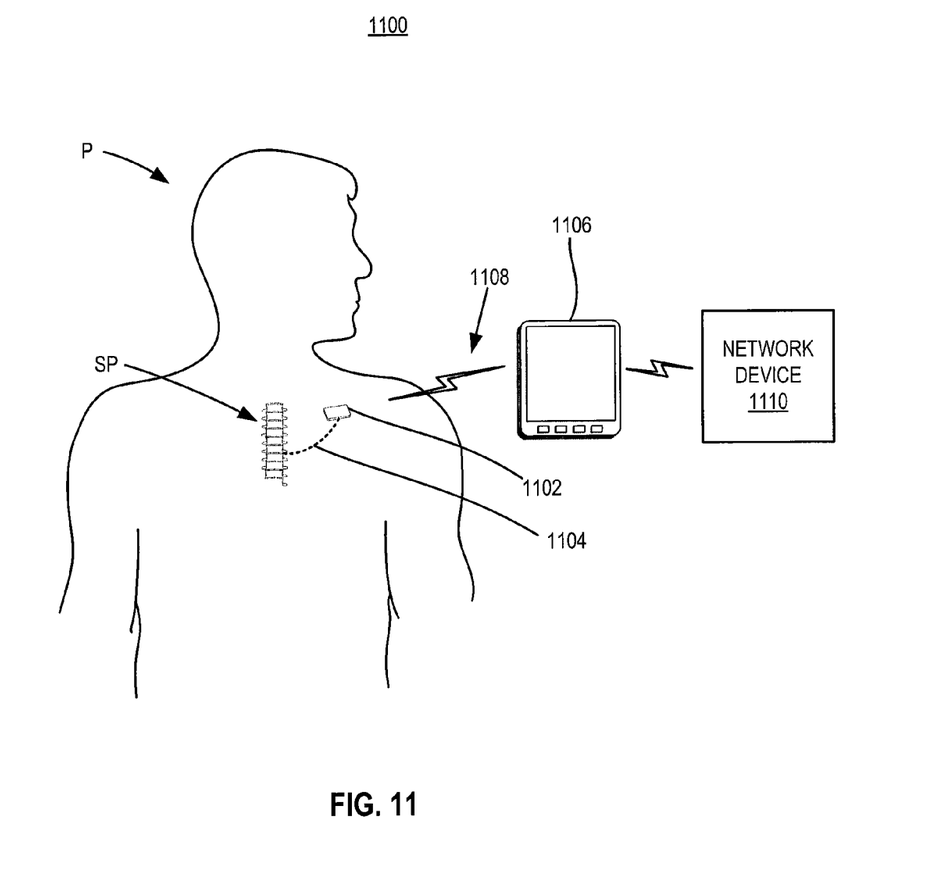
FIG. 11 is a simplified diagram of an embodiment of a medical system comprising an external device in communication with a neurostimulation patch to control neurostimulation for a patient.

FIG. 11 illustrates an example of a medical system 1100 including a neurostimulation patch 1102. In the illustrated example, the patch 1102 includes or is communicatively coupled to one or more implantable leads 1104 that are routed to the nervous system of the patient P. The patch 1102 may be configured and implanted to stimulate the spinal cord SP, the vagus nerve, baroreceptors, subcutaneous nerves, or other sections of the nervous system of the patient P.

The patch 1102 generates a stimulation signal (e.g., one or more pulses) and applies that stimulation signal to the designated section(s) of the nervous system. One or more of the stimulation signal characteristics, the stimulation timing, and the stimulation target areas may be programmed into the patch 1102. To this end, FIG. 11 illustrates an implementation where the patch 1102 communicates with an external device 1106. The patch 1102 and the external device 1106 may communicate with one another via a wireless communication link 1108 (as represented by the depicted wireless symbol).

The external device 1106 may take various forms. For example, the external device 1106 may be a base station, a programmer, a home safety monitor, a personal monitor, a follow-up monitor, a wearable monitor, or some other type of device that is configured to communicate with the patch 1102.

The communication link 1108 may be used to transfer information between devices in conjunction with various applications such as remote programming, remote home-monitoring, clinical visits, data acquisition, remote follow-up, and portable or wearable patient monitoring/control systems. For example, information may be transferred between the patch 1102 and the external device 1106 when the patient P is at a location that is relatively close to the external device 1106. Here, information transfers may be invoked upon command, at designated times, or in some other manner.

The external device 1106 may communicate with another device (e.g., that may provide a more convenient means for a physician or other personnel to program the patch 1102 or review information uploaded from the patch 1102), and vice versa. For example, personnel may use the network device 1110 to program the patch 1102 (e.g., to program neurostimulation parameters, to directly control neurostimulation, etc.). Conversely, the external device 1106 may send information to the network device 1110 (e.g., via a web server). In this way, monitoring personnel (e.g., a physician) may remotely access the information (e.g., by accessing a website). The monitoring personnel may then review the information uploaded from the external device 1106 to determine whether medical intervention is warranted.

It should be appreciated that various modifications may be incorporated into the disclosed embodiments based on the teachings herein. For example, the structure and functionality taught herein may be incorporated into types of devices other than the specific types of devices described above. Also, a patch may be constructed of materials and include components other than those specifically described herein.

In addition, the functionality described herein may be implemented in a variety of ways. For example, neurostimulation control (e.g., triggers) may take various forms. In some embodiments, a neurostimulation patch includes user interface circuitry that enables a person to program the desired neurostimulation parameters into a memory device included in the patch and/or to otherwise control the patch. In some embodiments, another device communicates with a patch (e.g., via a wireless connection or a temporary wired connection) to program the patch.

Different embodiments of an apparatus (e.g., device) as taught herein may include a variety of hardware and software processing components. In some embodiments, hardware components such as processors, controllers, state machines, logic, or some combination of these components, may be used to implement one or more of the described components, circuits, or functions.

In some embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

Moreover, some of the operations described herein may be performed by a device that is located externally with respect to the body of the patient. For example, an implanted device may send raw data or processed data to an external device that then performs the necessary processing.

The components and functions described herein may be connected or coupled in many different ways. The manner in which this is done may depend, in part, on whether and how the components are separated from the other components. In some embodiments, some of the connections or couplings represented by the lead lines in the drawings may be in an integrated circuit, on a circuit board or implemented as discrete wires or in other ways.

The signals discussed herein may take various forms. For example, in some embodiments a signal may comprise electrical signals transmitted over a wire, light pulses transmitted through an optical medium such as an optical fiber or air, or RF waves transmitted through a medium such as air, and so on. In addition, a plurality of signals may be collectively referred to as a signal herein. The signals discussed above also may take the form of data. For example, in some embodiments an application program may send a signal to another application program. Such a signal may be stored in a data memory.

Moreover, the recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

Also, it should be understood that any reference to elements herein using a designation such as "first," "second," and so forth does not generally limit the quantity or order of those elements. Rather, these designations may be used herein as a convenient method of distinguishing between two or more different elements or instances of an element. Thus, a reference to first and second elements does not mean that only two elements may be employed there or that the first element must precede the second element in some manner. Also, unless stated otherwise, a set of elements may comprise one or more elements. In addition, terminology of the form "at least one of A, B, or C" or "one or more of A, B, or C" or "at least one of the group consisting of A, B, and C" used in the description or the claims means "A or B or C or any combination of these elements." For example, this terminology may include A, or B, or C, or A and B, or A and C, or A and B and C, or 2A, or 2B, or 2C, and so on.

As used herein, the term "determining" encompasses a wide variety of actions. For example, "determining" may include calculating, computing, processing, deriving, investigating, looking up (e.g., looking up in a table, a database or another data structure), ascertaining, and the like. Also, "determining" may include receiving (e.g., receiving information), accessing (e.g., accessing data in a memory), and the like. Also, "determining" may include resolving, selecting, choosing, establishing, and the like.

In some aspects, an apparatus or any component of an apparatus may be configured to (or operable to or adapted to) provide functionality as taught herein. This may be achieved, for example: by manufacturing (e.g., fabricating) the apparatus or component so that it will provide the functionality; by programming the apparatus or component so that it will provide the functionality; or through the use of some other suitable implementation technique.

While certain embodiments have been described above in detail and shown in the accompanying drawings, it is to be understood that such embodiments are merely illustrative of and not restrictive of the teachings herein. In particular, it should be recognized that the teachings herein apply to a wide variety of apparatuses and methods. It will thus be recognized that various modifications may be made to the illustrated embodiments or other embodiments, without departing from the broad scope thereof. In view of the above, it will be understood that the teachings herein are intended to cover any changes, adaptations or modifications which are within the scope of the disclosure.

What is claimed is:

1. A neurostimulation system for stimulating a nervous system of a patient, comprising:
   a patch attachable to the skin of the patient, the patch including a body member comprising a substantially flat bottom portion;
   a neurostimulation circuit located within the body member of the patch, the neurostimulation circuit configured to radiate optical energy; and
   a stimulation lead subcutaneously implanted in the patient, the stimulation lead having a first end and a second end, with first end implanted proximate the target area of the patient to be stimulated, and the second end implanted subcutaneously in the patient proximate the patch; and
   a lens positioned in the body member of the patch and connected to the neurostimulation circuit, the lens to facilitate transmission of optical energy from the neurostimulation circuit through the skin of the patient to the second end of the stimulation lead.

2. The neurostimulation system of claim 1, wherein the second end of the stimulation lead includes a receiver configured to receive the optical energy radiated by the neurostimulation circuit.

3. The neurostimulation system of claim 2, wherein the receiver generates electrical signals based on the received optical energy.

4. The neurostimulation system of claim 2, wherein the first end of the stimulation lead includes electrodes and further wherein the stimulation lead includes conductors connecting the electrodes at the first end of the stimulation lead to receiver at the second end of the stimulation lead.

5. The neurostimulation system of claim 2, wherein the body member further comprises a top cover member above the chamber; and
   the top cover member is at least partially removable from the body member to allow removal of the neurostimulation circuit from the chamber.

* * * * *